United States Patent [19]
Cluff et al.

[11] Patent Number: 6,143,951
[45] Date of Patent: Nov. 7, 2000

[54] ALFALFA LINE CALLED WL-C290 AND METHOD FOR PRODUCING SAME

[75] Inventors: Gregory Jon Cluff; Franklin Louis Bedard, both of Bakersfield, Calif.

[73] Assignee: AgriBio Tech., Inc., Henderson, Nev.

[21] Appl. No.: 08/996,965

[22] Filed: Dec. 23, 1997

[51] Int. Cl.$^7$ .............................. A01H 5/00; A01H 4/00; A01H 1/04; A01H 5/10

[52] U.S. Cl. ...................... 800/298; 800/265; 800/274; 800/303; 435/420; 435/421

[58] Field of Search .................................. 800/298, 265, 800/274, 303; 435/420, 421

[56] References Cited

U.S. PATENT DOCUMENTS

| | | | |
|---|---|---|---|
| 5,075,217 | 12/1991 | Weber | 435/6 |
| 5,324,631 | 6/1994 | Helentjaris et al. | 435/6 |
| 5,324,646 | 6/1994 | Buising et al. | 435/172.3 |
| 5,364,759 | 11/1994 | Caskey et al. | 435/6 |
| 5,385,835 | 1/1995 | Helentjaris et al. | 435/172.3 |
| 5,451,705 | 9/1995 | Larkins et al. | 800/200 |
| 5,492,547 | 2/1996 | Johnson | 47/58 |
| 5,574,210 | 11/1996 | Saghai-Maroof et al. | 800/200 |
| 5,582,979 | 12/1996 | Weber | 435/6 |
| 5,675,066 | 10/1997 | Stucker | 800/200 |

OTHER PUBLICATIONS

"Standard Tests to Characterize Alfalfa Cultivars", *North Alfalfa Improvement Conference*, 3rd Edition, D1 to A8, (1996).

Armstrong, C., et al., "Establishmentand Maintenance of Friable, Embryogenic Maize Callus and the Involvement of L–Proline", *Planta*, 164, 207–214, (1985).

Bedard, F., "A Whitefly Wipeout", *Haymaker*, 11, (Spring 1992).

Behling, A., "New Alfalfa Germplasm Resists Whitefields", *Hay & Forage Grower*, 6, (Mar. 1997).

Bingham, E., et al., "Breeding Alfalfa which Regenerates from Callus Tissue in Culture", *Crop Science, 15*, 719–721, (1975).

Chu, C., et al., "Establishment of an Efficient Medium for Another Culture of Rice ThroughComparative Experiments on the Nitrogen Sources", *Scientia Sinica, 18*, 659–668, (Sep.–Oct. 1975).

Duvick, D., "Genetic Contributions to Yoeld Gains of U.S. Hybrid Maize, 1930–1980", *Genetic Contributions ato Yield Gains of Five Major Crop Plants*, W.R. Fehr, ed., CSSA Special Publication No. 7, 15–47, (1981).

Finkle, B., et al., "Growth and Regeneration of Alfalfa Callus Lines After Freezing in Liquid Mitrogen", *Plant Science, 42*, 133–140, (1985).

Goodman, M., et al., "Genetic Identification of Lines and Crosses Using Isoenzyme Electrophoresis", *Report of 35th Annual Corn and Sorghum Research Conference*, Chicago, IL, 10–31, (Dec. 9–11, 1980).

Gordan–Kamm, W., et al., "Transformation of Maize Cells and Regeneration of Fertile Transgenic Plants", *The Plant Cells, 2*, 603–618, (1990).

Hauptmann, R., et al., "Evaluation of Selectable Markers for Obtaining Stable Transformants in the Gramineae", *Plant Physiology, 86*, 602–606, (1988).

Hernandez–Fernandez, M., et al., "Inheritance of Somatic Embryogenesis in Alfalfa (Medicago sativa L.)", *Genome, 32*, 318–321, (1989).

Klein, T., et al., "Genetic Transformation of Maize Cells by Particle Bombardment", *Plant Physiology, 91*, 440–444, (1989).

Lee, M., "Inbred Lines of Maize and Their Molecular Markers", *The Maize Handbook*, Freeling, et al., eds., Springer–Verlag, New York., 423–432, (1994).

Murashige, T., et al., "A Revised Medium for Rapid Growth and Bio Assays with Tobacco Tissue Cultures", *Physiologia Plantarum, 15*, 473–497, (1962).

Ray, I., et al., "Cell Biology & Molecular Genetics: Breeding Diploid Alfalfa for Regeneration from Tissue Culture", *Crop Science, 29*, 1545–1548, (1989).

Rhodes, C., et al., "Genetically Transformed Maize from Protoplasts", *Science, 240*, 204–207, (1988).

Roberts, R., "Restriction and Modification Enzymes and Their Recognition Sequences", *Nucleic Acids Research, 10*, r117–r144, (1982).

Seitz Kris, M., et al., "Interactions of Highly Regenerative Genotypes of Alfalfa (Medicago Sativa) and Tissue Culture Protocols", *In Vitro Cellular & Developmental Biology, 24*, 1047–1052, (1988).

Teuber, L., et al., "Breeding Alfalfa for Resistance to the Silverleaf Whitefly", *Proceedings: 27th California Alfalfa Symposium*, Visalia, CA, 179–188, (Dec. 10–11, 1997).

Troyer, A., "A Retrospective View of Corn Genetic Resources", *The Journal of Heredity, 81*, 17–24, (1990).

Withers, L., et al., "Proline: A Novel Cryoprotectant for the FreezePreservation of Cultured Cells of Zea mays L.", *Plant Physiology, 64*, 375–378, (1979).

Elgin et al. (1985) Inheritance of Resistance to Race 1 and Race 2 Anthracnose in Arc and Saranac AR Alfalfa, Crop Science, 25, pp. 861–865.

Elgin et al. (1983) Use of Strain Crosses in the Development of Multiple Pest resistant Alfalfa with Improved Field performance, Crop Science, 23, pp. 57–64.

Elgin (1979) Inheritance of Stem–Nematoe resistance in Alfalfa, Crop Science, 19, pp. 352–354.

(List continued on next page.)

*Primary Examiner*—David T. Fox
*Assistant Examiner*—Anne Marie Grünberg
*Attorney, Agent, or Firm*—Schwegman, Lundberg, Woessner & Kluth PA

[57] ABSTRACT

An improved synthetic alfalfa variety called WL-C290, and method for producing same. The present invention provides a hot-weather, i.e., Dormancy Group 10 type, very non-dormant synthetic alfalfa variety, wherein one embodiment is named WL-C290, that provides improved yields under a variety of environmental conditions and, in particular, better resistance to silverleaf whitefly pests. The primary uses of this WL-C290 variety are hay, haylage, greenchop and dehydrated feed for livestock.

26 Claims, 13 Drawing Sheets

(2 of 13 Drawing Sheet(s) Filed in Color)

OTHER PUBLICATIONS

Bedard (1992) A Whitefly Wipeout, Haymaker, p. 11.

Smith et al. (1995) Morphological and Agronomic Affinities among Middle Eastern Alfalfas–Accessions from Oman and Yemen, Crop Science, 35, pp. 1188–1194.

Woodward et al. (1988) Registration of '5929' Alfalfa, Crop Science, 28, p. 186.

Hanson et al. (1987) Registration of 'WL605' A;fa;fa, Crop Science, 27, p. 1084.

Fehr (1987) Principles of Cultivar Development, McGraw–Hill, Inc, pp. 152–153, 422–423, 60.

Staub et al. (1996) Genetic Markers, Map Construction, and Their Application in Plant Breeding, Hort Science, 31(5), pp. 729–738.

Fuentes et al (1993), Plant Cell Tissue Organ Colt, 34(3):299–302.

Fusarium Wilt
Test Conducted by W-L Research at Evansville, WI

| Variety | Resistance Class | Syn Gen | Unadjusted % R | Adjusted % R | Score or A.S.I. |
|---|---|---|---|---|---|
| 1. Test variety WL-C290 | HR | 1 | 48 | 58 | 2.32 |
| 2. Agate | HR | | 45 | 54 | 2.28 |
| 3. Mn GN-1 | S | | 6 | 6 | 4.46 |
| Test Mean: | | | 33 | | 3.02 |
| L.S.D. (.05) | | | 20 | | 0.60 |
| C.V. (%) (coefficient of variation) | | | 23 | | 17.20 |

Test conducted in field space-plant nursery.

FIG. 2A

Phytophthora Root Rot
Test Conducted by W-L Research at Evansville, WI

| Variety | Resistance Class | Syn Gen | Unadjusted % R | Adjusted % R | Score or A.S.I. |
|---|---|---|---|---|---|
| 1. Test Variety | R | 1 | 30 | 35 | |
| 2. Mn PD-1 | R | | 39 | 46 | |
| 3. Saranac | S | | 0 | 0 | |
| Test Mean: | | | 23 | | |
| L.S.D. (0.5) | | | 11 | | |
| C.V. (%) (coefficient of variation) | | | 22 | | |

Test conducted in Lab Greenhouse.

FIG. 2B

Stem Nematode
Test Conducted by W-L Research at Warden, WA

| Variety | Resistance Class | Syn Gen | Unadjusted % R | Adjusted % R | Score or A.S.I. |
|---|---|---|---|---|---|
| 1. Test variety | R | 1 | 32 | 37 | 3.4 |
| 2. Lew | R | | 28 | 32 | 3.5 |
| 3. Moapa 69 | S | | 1 | 1 | 4.4 |
| Test Mean: | | | | 20 | 3.7 |
| L.S.D. (.05) | | | | 11 | 0.3 |
| C.V. (%) (coefficient of variation) | | | | 23 | 7.0 |

Test conducted in Lab Greenhouse.

FIG. 2C

Pea Aphid
Test Conducted by W-L Research at Bakersfield, CA

| Variety | Resistance Class | Syn Gen | Unadjusted % R | Adjusted % R | Score or A.S.I. |
|---|---|---|---|---|---|
| 1. Test variety | HR | 1 | 46 | 60 | 2.7 |
| 2. Cuf 101 | HR | | 42 | 55 | 3.2 |
| 3. Caliverde | S | | 3 | 4 | 4.7 |
| Test Mean: | | | | 30 | 3.5 |
| L.S.D. (.05) | | | | 3 | 0.4 |
| C.V. (%) (coefficient of variation) | | | | 5 | 9.5 |

Test conducted in Lab Greenhouse.

FIG. 2D

Spotted Alfalfa Aphid
Test Conducted by W-L Research at Bakersfield, CA

| Variety | Resistance Class | Syn Gen | Unadjusted % R | Adjusted % R | Score or A.S.I. |
|---|---|---|---|---|---|
| 1. Test variety | R | 1 | 35 | 36 | 3.5 |
| 2. CUF 101 | HR | | 59 | 60 | 2.5 |
| 3. Caliverde | S | | 0 | 0 | 5.0 |
| Test Mean: | | | 31 | | 3.6 |
| L.S.D. (.05) | | | 10 | | 0.4 |
| C.V. (%) (coefficient of variation) | | | 14 | | 9.1 |

Test conducted in Lab Greenhouse.

FIG. 2E

Blue Alfalfa Aphid
Test Conducted by W-L Research at Bakersfield, CA

| Variety | Resistance Class | Syn Gen | Unadjusted % R | Adjusted % R | Score or A.S.I. |
|---|---|---|---|---|---|
| 1. Test variety | HR | 1 | 56 | | 2.5 |
| 2. Cuf 101 | HR | | 55 | | 2.5 |
| 3. Caliverde | S | | 5 | | 5.0 |
| Test Mean: | | | 39 | | 3.3 |
| L.S.D. (.05) | | | 1 | | 0.2 |
| C.V. (%) (coefficient of variation) | | | 2 | | 6.2 |

Test conducted in Lab Greenhouse.

FIG. 2F

Root-Knot Nematode – Species: *M. hapla* (Northern)
Test Conducted by W-L Research at Warden, WA

| Variety | Resistance Class | Syn Gen | Unadjusted % R | Adjusted % R | Score or A.S.I. |
|---|---|---|---|---|---|
| 1. Test variety | HR | 1 | 57 | 56 | 2.0 |
| 2. Syn XX | HR | | 92 | 90 | 1.2 |
| 3. Lahaontan | S | | 7 | 7 | 3.7 |
| Test Mean: | | | 52 | | 2.3 |
| L.S.D. (.05) | | | 15 | | 0.5 |
| C.V. (%) (coefficient of variation) | | | 24 | | 16.0 |

Test conducted in Lab Greenhouse.

FIG. 2G

Root-Knot Nematode – Species: *Meloidogyne incognita* (Southern)
Test Conducted by ___ Crop Characteristics ___ at Farmington, MN

| Variety | Resistance Class | Syn Gen | Unadjusted % R | Adjusted % R | Score or A.S.I. |
|---|---|---|---|---|---|
| 1. Test variety | HR | 1 | 54 | 55 | 1.6 |
| 2. Moapa 69 | HR | | 49 | 50 | 1.7 |
| 3. Lahaontan | S | | 1 | 1 | 3.0 |
| Test Mean: | | | 35 | | 2.1 |
| L.S.D. (.05) | | | 7 | | 0.2 |
| C.V. (%) (coefficient of variation) | | | 14 | | 6.9 |

Test conducted in Lab Greenhouse.

FIG. 2H

Other Pest Evaluations (Silverleaf Whitefly) *Bemisia argentifolii*
Nymphal Density Score*
Test Conducted by W-L Research at Westmorland, CA

| Variety | Resistance Class | Syn Gen | Unadjusted % R | Adjusted % R | Score or A.S.I. |
|---|---|---|---|---|---|
| 1. Test variety | R | 1 | 42 | | 2.8 |
| 2. Cibola | S | | 1 | | 4.1 |
| 3. CUF 101 | S | | 0 | | 4.4 |
| Test Mean: | | | 15 | | 3.8 |
| L.S.D. (.05) | | | 17 | | 0.3 |
| C.V. (%) (coefficient of variation) | | | 79 | | 6.3 |

Test conducted in field Replicated Nursery.

* No standard test is currently available for resistance to silverleaf whitefly; nymphal density score is the most descriptive resistance measurement available for this pest.

FIG. 2I

Bacterial Wilt
Test Conducted by W-L Research at Evansville, WI

| Variety | Resistance Class | Syn Gen | Unadjusted % R | Adjusted % R | Score or A.S.I. |
|---|---|---|---|---|---|
| 1. Test variety WL-C290 | S | 1 | 4 | 5 | 3.47 |
| 2. Vernal | R | | 32 | 42 | 2.15 |
| 3. Sonora | S | | 0 | 0 | 3.47 |
| Test Mean: | | | 12 | | 3.03 |
| L.S.D. (.05) | | | 11 | | 0.25 |
| C.V. (%) (coefficient of variation) | | | 14.7 | | 7.8 |

Test conducted in field space-plant nursery

FIG. 2J

Anthracnose
Test Conducted by W-L Research at Evansville, WI

| Variety | Resistance Class | Syn Gen | Unadjusted % R | Adjusted % R |
|---|---|---|---|---|
| 1. Test variety WL-C290 | S | 1 | 0 | 0 |
| 2. ARC | R |  | 57 | 65 |
| 3. Saranac | S |  | 1 | 1 |
| Test Mean: |  |  | 19 | 22 |
| L.S.D. (.05) |  |  | 10 | 11 |
| C.V. (%) (coefficient of variation) |  |  | 30.6 | 29 |

Test conducted in lab greenhouse.

FIG. 2K

Westmorland Year 19 Results
3' × 14' Plots Seeded: November 2, Year 18
4 Replications

| Entry | Tons Air-Dry Hay/Acre (rank within harvest) | | | | | Total | % Check |
| --- | --- | --- | --- | --- | --- | --- | --- |
| | April 28 | May 28 | June 25 | Oct. 2 | Nov. 13 | | |
| B-147 (WL-C290) | 1.48(21) | 1.66(12) | 1.89(3) | 1.14(1) | 0.82(1) | 6.99 | 109 |
| B-109 (C244) | 1.62(2) | 1.74(3) | 1.92(1) | 0.90(3) | 0.62(4) | 6.80 | 106 |
| CIBOLA | 1.58(7) | 1.76(1) | 1.85(9) | 0.88(5) | 0.58(8) | 6.64 | 103 |
| CUF 101 | 1.54(13) | 1.62(20) | 1.86(8) | 0.90(3) | 0.66(3) | 6.58 | 102 |
| WL 525 HQ | 1.69(1) | 1.74(2) | 1.90(2) | 0.67(23) | 0.51(18) | 6.52 | 101 |
| MECCA II | 1.60(3) | 1.73(4) | 1.78(16) | 0.80(8) | 0.58(7) | 6.50 | 101 |
| B-293 (C294) | 1.43(24) | 1.66(14) | 1.88(5) | 0.88(6) | 0.60(5) | 6.46 | 101 |
| CORONADO | 1.54(12) | 1.66(13) | 1.88(4) | 0.80(9) | 0.55(11) | 6.44 | 100 |
| WL 612 | 1.58(6) | 1.70(8) | 1.84(11) | 0.74(14) | 0.55(10) | 6.42 | 100 |
| B-203 (C249) | 1.57(8) | 1.71(7) | 1.80(13) | 0.74(15) | 0.56(9) | 6.38 | 99 |
| PIO 5939 | 1.59(5) | 1.65(17) | 1.83(12) | 0.73(17) | 0.55(11) | 6.35 | 99 |
| B-296 (C243) | 1.50(18) | 1.64(18) | 1.85(9) | 0.79(10) | 0.53(15) | 6.31 | 98 |
| B-143 (C248) | 1.55(11) | 1.65(16) | 1.71(22) | 0.77(11) | 0.59(6) | 6.27 | 98 |
| B-95 (91-224-F) | 1.48(20) | 1.68(10) | 1.73(20) | 0.81(7) | 0.55(13) | 6.25 | 97 |
| B-220 (W135) | 1.50(17) | 1.68(10) | 1.88(6) | 0.71(19) | 0.47(22) | 6.25 | 97 |
| B-187 (C153) | 1.51(15) | 1.61(21) | 1.79(15) | 0.76(12) | 0.54(14) | 6.22 | 97 |
| B-280 (C155) | 1.57(9) | 1.72(6) | 1.68(24) | 0.72(18) | 0.51(19) | 6.19 | 96 |
| B-259 (C291) | 1.59(4) | 1.66(15) | 1.70(23) | 0.74(13) | 0.47(23) | 6.16 | 96 |
| KERN | 1.49(19) | 1.68(9) | 1.87(7) | 0.61(26) | 0.46(24) | 6.11 | 95 |
| B-221 (C245) | 1.53(14) | 1.60(22) | 1.74(18) | 0.69(20) | 0.52(16) | 6.09 | 95 |
| B-199 (C171) | 1.56(10) | 1.72(5) | 1.67(25) | 0.68(22) | 0.45(25) | 6.08 | 95 |
| B-292 (C250) | 1.44(23) | 1.62(19) | 1.72(21) | 0.73(16) | 0.50(21) | 6.02 | 94 |
| B-16 (W222) | 1.48(21) | 1.57(25) | 1.74(19) | 0.66(24) | 0.52(17) | 5.96 | 93 |
| B-278 (C293) | 1.40(25) | 1.59(24) | 1.77(17) | 0.68(21) | 0.50(20) | 5.95 | 93 |
| B-272 (C167) | 1.51(16) | 1.59(23) | 1.80(14) | 0.62(25) | 0.42(26) | 5.95 | 93 |
| HASAWI | 1.16(26) | 1.19(26) | 1.50(26) | 0.94(2) | 0.69(2) | 5.49 | 86 |
| MEAN | 1.52 | 1.65 | 1.79 | 0.77 | 0.55 | 6.28 | |
| LSD @ .05 | 0.21 | 0.19 | 0.22 | 0.15 | 0.10 | 0.61 | |
| .01 | 0.28 | 0.25 | 0.29 | 0.20 | 0.14 | 0.81 | |
| CV% | 9.89 | 8.03 | 8.75 | 13.53 | 13.30 | 6.86 | |

FIG. 3A

Bakersfield Year 19 Results
3' × 14' Plots Seeded: November 2, Year 18
4 Replications

| Entry | Tons Air-Dry Hay/Acre (Yield rank within harvest) | | | | Total | % Check |
|---|---|---|---|---|---|---|
| | July 21 | Aug. 23 | Sept. 23 | Oct. 24 | | |
| B-147 (WL-C290) | 2.00(16) | 1.70(2) | 1.49(1) | 1.81(1) | 6.99 | 107 |
| B-95 (91-224-F) | 2.18(1) | 1.74(1) | 1.46(2) | 1.52(10) | 6.90 | 106 |
| B-221 (C245) | 2.09(5) | 1.69(3) | 1.44(3) | 1.56(4) | 6.77 | 104 |
| MECCA II | 2.13(3) | 1.68(4) | 1.40(7) | 1.51(11) | 6.72 | 103 |
| CORONADO | 2.06(9) | 1.63(13) | 1.39(13) | 1.54(6) | 6.62 | 102 |
| B-16 (W222) | 2.06(7) | 1.63(15) | 1.39(12) | 1.51(12) | 6.59 | 101 |
| B-293 (C294) | 1.96(26) | 1.64(11) | 1.43(4) | 1.55(5) | 6.58 | 101 |
| B-291 (C252) | 1.99(17) | 1.66(6) | 1.39(11) | 1.52(9) | 6.56 | 101 |
| B-5 (93-25) | 2.05(12) | 1.64(12) | 1.39(10) | 1.47(16) | 6.55 | 101 |
| PIO 5939 | 2.06(7) | 1.63(14) | 1.40(8) | 1.44(20) | 6.53 | 100 |
| WL 516 | 2.08(6) | 1.65(8) | 1.36(15) | 1.42(26) | 6.51 | 100 |
| WL 525 HQ | 1.98(19) | 1.67(5) | 1.40(6) | 1.45(19) | 6.51 | 100 |
| CORONA | 2.14(2) | 1.64(10) | 1.35(22) | 1.37(29) | 6.51 | 100 |
| B-256 (93-226) | 2.04(13) | 1.65(9) | 1.35(18) | 1.43(24) | 6.47 | 99 |
| WL 612 | 1.98(20) | 1.55(29) | 1.34(27) | 1.60(2) | 6.47 | 99 |
| B-296 (C243) | 1.96(23) | 1.61(18) | 1.40(8) | 1.50(14) | 6.47 | 99 |
| B-292 (C250) | 1.98(21) | 1.66(7) | 1.36(17) | 1.44(20) | 6.44 | 99 |
| B-120 (93-219) | 1.99(17) | 1.60(22) | 1.34(23) | 1.51(13) | 6.43 | 99 |
| B-272 (C167) | 1.97(22) | 1.61(20) | 1.36(16) | 1.49(15) | 6.43 | 99 |
| DK 189 | 2.05(11) | 1.61(18) | 1.32(28) | 1.44(23) | 6.42 | 99 |
| MARICOPA | 2.10(4) | 1.62(16) | 1.29(32) | 1.40(28) | 6.41 | 98 |
| B-220 (W135) | 1.94(27) | 1.55(28) | 1.34(25) | 1.54(6) | 6.38 | 98 |
| B-278 (C293) | 1.90(32) | 1.60(21) | 1.41(5) | 1.46(18) | 6.37 | 98 |
| CONDOR | 1.96(25) | 1.59(23) | 1.37(14) | 1.44(22) | 6.36 | 98 |
| B-280 (C155) | 1.93(29) | 1.59(25) | 1.35(20) | 1.46(17) | 6.34 | 97 |
| B-109 (C244) | 1.88(33) | 1.56(26) | 1.34(24) | 1.53(8) | 6.30 | 97 |
| B-143 (C248) | 1.87(34) | 1.53(31) | 1.31(29) | 1.58(3) | 6.29 | 97 |
| B-264 (C146) | 1.90(31) | 1.59(23) | 1.35(19) | 1.42(27) | 6.27 | 96 |
| KERN | 2.06(10) | 1.52(33) | 1.34(25) | 1.30(31) | 6.21 | 95 |
| B-14 (C247) | 1.96(24) | 1.56(27) | 1.35(21) | 1.34(30) | 6.20 | 95 |
| WL 457 | 2.01(14) | 1.61(17) | 1.30(30) | 1.25(32) | 6.17 | 95 |
| B-203 (C249) | 1.90(30) | 1.53(30) | 1.30(30) | 1.42(25) | 6.16 | 95 |
| 13R SUPREME | 1.94(28) | 1.47(34) | 1.23(33) | 1.21(33) | 5.86 | 90 |
| B-65 (91-210) | 2.00(15) | 1.52(32) | 1.20(34) | 1.13(34) | 5.85 | 90 |
| MEAN | 2.00 | 1.61 | 1.36 | 1.46 | 6.43 | |
| LSD @ .05 | 0.18 | 0.12 | 0.09 | 0.19 | 0.42 | |
| .01 | 0.24 | 0.16 | 0.12 | 0.25 | 0.56 | |
| CV% | 6.44 | 5.29 | 4.64 | 9.12 | 4.62 | |

FIG. 3B

ALFALFA LINE CALLED WL-C290 AND METHOD FOR PRODUCING SAME

FIELD OF THE INVENTION

This invention relates to the field of alfalfa plants, and more specifically to an improved synthetic alfalfa variety and a method for producing such a synthetic variety.

BACKGROUND OF THE INVENTION

Alfalfa (*Medicago sativa*) is an important and valuable forage and feed crop throughout the world. Alfalfa exhibits traits setting it apart from many other crop plants. It is an auto-tetraploid and is frequently self-incompatible in breeding. When selfed, little or no seed is produced, or the seed may not germinate, or when it does, it may later stop growing. Typically, fewer than five percent of selfed crosses produce seed. When a very small population is crossbred, inbreeding depression occurs, and traits of interest, such as quality, yield, and resistance to a large number of pests (e.g., seven or eight different pests), are lost. Thus, producing a true breeding parent for hybrids is not possible, which complicates breeding substantially.

Some sources indicate that there are nine major germplasm sources of alfalfa: *M. falcata*, Ladak, *M. varia*, Turkistan, Flemish, Chilean, Peruvian, Indian, and African. Tissue culture of explant source tissue, such as mature cotyledons and hypocotyls, demonstrates the regeneration frequency of genotypes in most cultivars is only about 10 percent. Seitz-Kris, M. H. and E. T. Bingham, In vitro *Cellular and Developmental Biology* 24 (10):1047–1052 (1988). Efforts have been underway to improve regeneration of alfalfa plants from callus tissue. E. T. Bingham, et. al., *Crop Science* 15:719–721 (1975). Some methods for regeneration of alfalfa plants from tissue culture are described in U.S. Pat. No. 5,324,646 issued Jun. 28, 1994, which is hereby incorporated by reference.

Additionally, researchers believe that somatic embryogenesis in alfalfa is inheritable, and is controlled by relatively few genes. Efforts at improving regeneration have thus been directed towards isolation of the genetic control of embryogenesis, and breeding programs which would incorporate such information. See, e.g., M. M. Hernandez-Fernandez, and B. R. Christie, *Genome* 32:318–321 (1989); I. M. Ray and E. T. Bingham, *Crop Science* 29:1545–1548 (1989).

SUMMARY OF THE INVENTION

The present invention provides an extremely non-dormant, Dormancy Group 10 type, synthetic alfalfa variety, wherein one embodiment is named WL-C290, that provides improved yields under a variety of environmental conditions and, in particular, better resistance to the insect pest silverleaf whitefly (*Bemisia argentifolii*). The primary uses of this WL-C290 variety are hay, haylage, greenchop and dehydrated feed for livestock. The present invention also provides a method for breeding and selecting alfalfa in order to obtain resistance or high resistance to certain alfalfa pests. In particular, this method obtains a very non-dormant alfalfa variety that is resistant to silverleaf whitefly.

In one embodiment, the present invention includes seed of synthetic alfalfa variety designated WL-C290 and having American Type Culture Collection (ATCC) Accession No. 209502. In another embodiment, the present invention includes an alfalfa plant or its parts produced by the seed of synthetic alfalfa variety designated WL-C290 or produced by regenerable plant parts of such seed. In yet other embodiments, the present invention includes pollen or an ovule of the plant produced by the seed of synthetic alfalfa variety designated WL-C290.

In another embodiment, the present invention includes an alfalfa plant having all the physiological and morphological characteristics of a population of plants produced by the seed of the synthetic alfalfa variety designated WL-C290. In another embodiment, the present invention includes a male sterile alfalfa plant otherwise having all the physiological and morphological characteristics of a population of plants produced by the seed of the synthetic alfalfa variety designated WL-C290.

In yet another embodiment, the present invention includes a tissue culture of regenerable cells of a synthetic variety alfalfa plant named WL-C290, wherein the tissue regenerates plants having all the morphological and physiological characteristics of the synthetic variety alfalfa plant named WL-C290, the seed of which have been deposited and have ATCC Accession No. 209502 (the ATCC is the American Type Culture Collection, 10801 University Boulevard, Manassas, Va. 20110-2209, 703-365-2700. In one such embodiment, the tissue culture is derived from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. In another such embodiment, the present invention includes an alfalfa plant regenerated from the above described tissue culture, having all the morphological and physiological characteristics of synthetic alfalfa variety WL-C290.

Another aspect of the present invention is a method for producing first-generation synthetic variety alfalfa seed, the method comprising crossing a first parent alfalfa plant with a second parent alfalfa plant and harvesting the resultant first-generation (F1) hybrid alfalfa seed, wherein said first or second parent alfalfa plant is the alfalfa plant produced by the seed of synthetic alfalfa variety designated WL-C290 or plant parts of such seed.

Yet another aspect of the present invention is a method for breeding and selecting alfalfa including the steps of: (a) crossing a non-dormant or extremely non-dormant alfalfa variety with an alfalfa variety that is resistant to silverleaf whitefly; and (b) growing alfalfa plants from germplasm resulting from the cross of step (a). In one such embodiment, this method further includes the steps of: (c) selecting from among the plants resulting from step (b) plants that are more resistant to silverleaf whitefly than other plants resulting from step (b); and (d) crossing the selected plants of step (c) amongst themselves.

Still another aspect of the present invention is a method for breeding and selecting alfalfa comprising the steps of: (a) selecting plants, derived from a Pioneer 5929 alfalfa line, for resistance to stem nematodes; (b) selecting plants, derived from a WL 605 alfalfa line, for resistance to stem nematodes and anthracnose; (c) crossing the selected plants of step (a) and step (b); (d) generating plants from germplasm resulting from step (c); (e) generating plants from a Hasawi alfalfa line; and (f) crossing the plants of step (d) and step (e). In one such embodiment, the crossing of step (f) is a two-population cross using the plants of step (d) as female parents and the plants of step (e) as male parents.

In another such embodiment, the method further includes the steps of: (g) generating plants from germplasm resulting from step (f); (h) selecting plants from among the plants of step (g), for resistance to spotted alfalfa aphid; and (i)

crossing the selected plants of step (h) amongst themselves. In yet another such embodiment, the method further includes the steps of: (j) generating plants from germplasm resulting from step (i); (k) selecting plants from among the plants of step (j), for resistance to silverleaf whitefly; and (l) crossing the selected plants of step (k) amongst themselves.

In one such embodiment, step (k) further comprises the substep of selecting plants for yield. In one such embodiment, the method further includes the steps of: (m) generating plants from germplasm resulting from step (l); (n) selecting plants from among the plants of step (m), for resistance to silverleaf whitefly and for vigor; and (o) crossing the selected plants of step (n) amongst themselves.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 2A is a table comparing the test variety WL-C290 to other alfalfa varieties for resistance to fusarium wilt.

FIG. 2B is a table comparing the test variety WL-C290 to other alfalfa varieties for resistance to phytophthora root rot.

FIG. 2C is a table comparing the test variety WL-C290 to other alfalfa varieties for resistance to stem nematode.

FIG. 2D is a table comparing the test variety WL-C290 to other alfalfa varieties for resistance to pea aphid.

FIG. 2E is a table comparing the test variety WL-C290 to other alfalfa varieties for resistance to spotted alfalfa aphid.

FIG. 2F is a table comparing the test variety WL-C290 to other alfalfa varieties for resistance to blue alfalfa aphid.

FIG. 2G is a table comparing the test variety WL-C290 to other alfalfa varieties for resistance to northern root knot nematode.

FIG. 2H is a table comparing the test variety WL-C290 to other alfalfa varieties for resistance to southern root knot nematode.

FIG. 2I is a table comparing the test variety WL-C290 to other alfalfa varieties for resistance to silverleaf whitefly.

FIG. 2J is a table comparing the test variety WL-C290 to other alfalfa varieties for resistance to bacterial wilt.

FIG. 2K is a table comparing the test variety WL-C290 to other alfalfa varieties for resistance to anthracnose.

FIG. 3A is a table comparing the test variety WL-C290 to other alfalfa varieties for yield in the Westmorland, Calif. area in year 19.

FIG. 3B is a table comparing the test variety WL-C290 to other alfalfa varieties for yield in the Bakersfield, Calif. area in year 19.

DESCRIPTION OF PREFERRED EMBODIMENTS

Figure 1A:
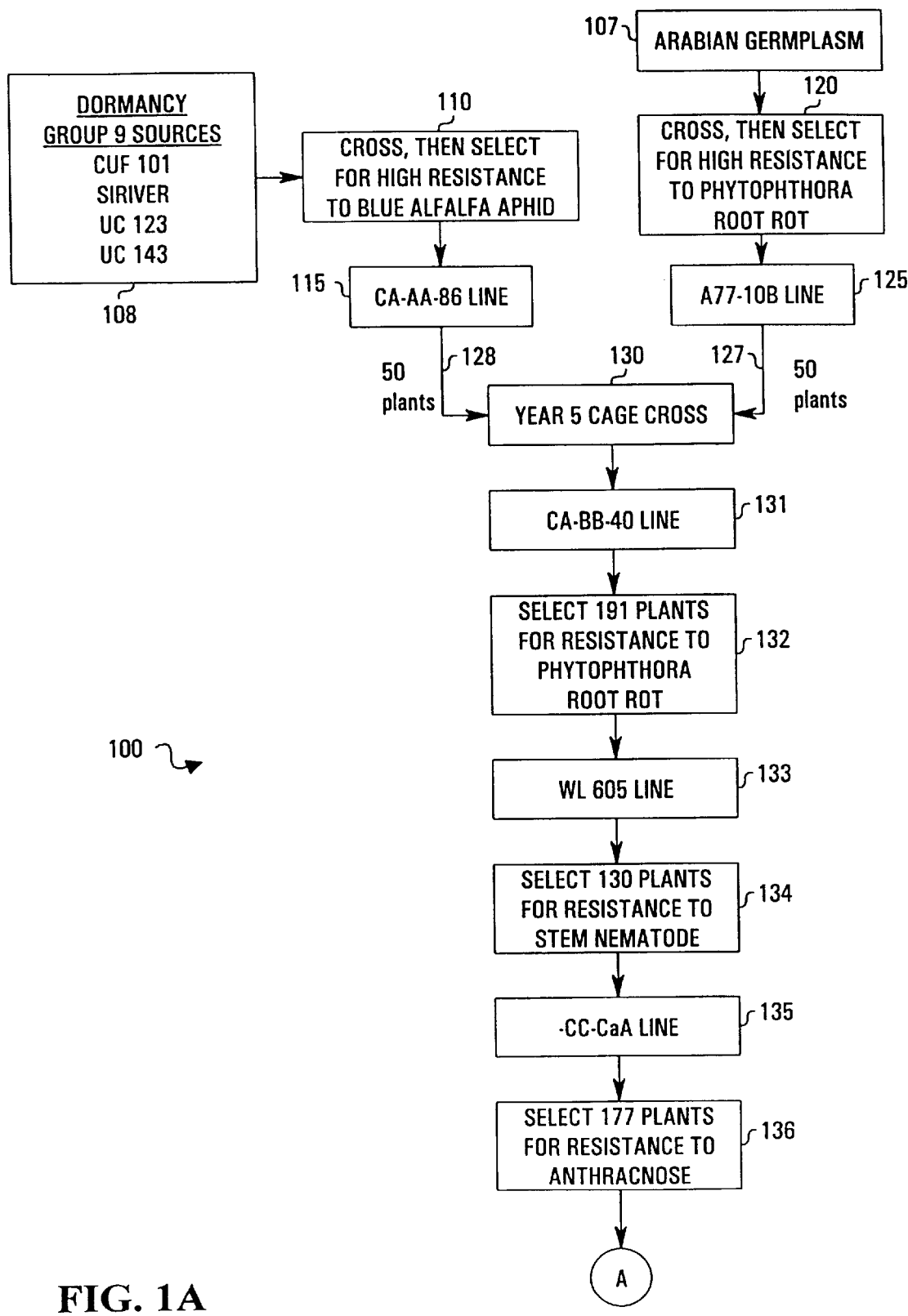
FIGS. 1A and 1B together form FIG. 1, which shows a schematic representation of the breeding and selecting process for one embodiment of the present invention having a goal of producing a Dormancy Group 10 alfalfa that is resistant to silverleaf whitefly.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The present invention provides an extremely non-dormant, i.e., Dormancy Group 10 type (suitable for hot-weather and very long growing seasons), synthetic alfalfa variety, wherein one embodiment is named WL-C290, that provides improved yields under a variety of environmental conditions and, in particular, better resistance to silverleaf whitefly pests.

Alfalfa is classified into fall dormancy groups, numbered 1 to 10, where Dormancy Group 1 is very dormant and suited for cold climates (such varieties would stop growing and go dormant over winter), and Dormancy Group 10 is very non-dormant and suited for very hot climates (such varieties would have high growth rates over a very long growing season and would have relatively high winter activity). Currently, the NAVRB (National Alfalfa Variety Review Board) recognizes standard or check varieties for Dormancy Groups 1–9, but does not have a standard check variety for Group 10. The check cultivars are listed in the NAAIC *Standard Tests to Characterize Alfalfa Cultivars*, 3rd Edition, as amended, 1995. (NAAIC is the North America Alfalfa Improvement Conference, which is the governing body over the NAVRB, (National Alfalfa Variety Review Board)). The check varieties for the various fall dormancy ratings/Dormancy Groups (corresponding to the rating scale used by the Certified Alfalfa Seed Council (CASC)) are as follows:

Dormancy Group 1—Norseman, Beaver, and Maverick
Dormancy Group 2—Vernal, Profit, and 526
Dormancy Group 3—Ranger, Oneida VR, and 5246
Dormancy Group 4—Saranac, Cutter, and Legend
Dormancy Group 5—Archer, Belmont, and Pike
Dormancy Group 6—ABI 700, Meteor
Dormancy Group 7—Dona Ana, Sutter
Dormancy Group 8—Maricopa, Pierce, 5715
Dormancy Group 9—CUF101, Mecca, 5929

As used herein, an alfalfa variety having Dormancy Group 10-type characteristics would have winter activity (i.e., winter growth rates) significantly greater than alfalfa variety CUF 101, one of the Dormancy Group 9 check varieties.

One way that commercial alfalfa seed is produced is as a synthetic variety. A synthetic variety is produced by multi-way cross-pollinating within a small number of plants. For the present invention, one method used (called single-population synthetic crossing) to place a population of plants, e.g., one hundred fifty to two hundred individual plants, under an enclosure (a "cage") that functions to exclude pollen from external sources. These plants are cross-pollinated using a captive population of bees such that the pollen parent and ovule parent are randomly selected by the bees only from among the, e.g., 200 parent plants. This process is called a "cage cross." For example, the 200 parent plants may have been selected for a particular trait, such as resistance to a particular pest, and by using such random cross-pollination from a selective population, and by repeating the selection of the most resistant plants across several generations crossed in this way, substantial improvements can be made in the traits of the germplasm. The seed produced is harvested as a bulk result from all 200 plants.

The term "germplasm" as used herein refers to the hereditary material or genes of a plant or population of plants. The term "germplasm" includes seeds, pollen and ovules from a variety, as well as to a tissue culture of regenerable cells and/or plants produced by such tissue culture, wherein the tissue culture is derived, in whole or in part, from a regenerable plant part, selected from the group consisting of leaves, roots, root tips, root hairs, anthers, pistils, stamens, pollen, ovules, flowers, seeds, embryos, stems, buds, cotyledons, hypocotyls, cells, protoplasts, chromosomes, or other genetic material of the variety.

In general, alfalfa is self-incompatible, and typically when a very small population is crossbred, suffers inbreeding depression, and traits of interest, such as quality, yield, and resistance to a large number of pests, are lost. Thus, when alfalfa is bred according to the present invention in a cage cross, preferably over one-hundred plants are used, and more preferably 175 to 200 plants are crossed, in order to avoid inbreeding depression, and to keep the resistances to all of the pests.

A cage cross, typically having 175 to 200 parent plants, typically produces one harvest of seeds per year, wherein all of the plants are cut off at the end of the growing season and run though a threshing machine to separate the seed. Typically, one to seven pounds of seeds are produced (with an average of four pounds). Typically, there are about 450 seeds per gram, or about 200,000 seeds per pound. If seeds are shipped to the southern hemisphere (or to a greenhouse) and planted, a second growing season, and a second generation or harvest of seeds can be obtained each year.

In another method used by the present invention (called two-population synthetic crossing), human pollinators (for example) cross-pollinate plants by hand, using pollen collected from 100 selected pollen parents to pollinate 100 selected ovule parents in a cage. In general, the ovule parents are self infertile and the cage prevents pollinating insects or wind from bringing in unwanted pollen, such that all or nearly all of the seed produced are the result of the intended cross.

Typically, a human pollinator will take a "boat" fabricated on the spot by chewing the end of a toothpick flat; pollen is collected from anthers of a single pollen-parent plant onto the wet flat end of the toothpick, and then deposited on the stigmas of a single ovule-parent plant. The toothpick is then discarded. Another toothpick is then made into a boat, and the next pair of plants is crossed, and this process is repeated for each respective pair of pollen and ovule parent plants.

In other embodiments, male-sterile ovule parent plants, or ovule parent plants which have had other steps taken to prevent pollination from their own pollen are used with bees or other pollinating animals used to transfer pollen from the pollen parent to the ovule parent, in order to save cost relative to using a human to perform the pollination operation. Two-population synthetic crossing allows traits from two parent populations to be cross-combined more efficiently than if random pollination were used among all 200 plants, since, for each seed produced, half the genes are contributed by the pollen parent from one population and the other half of the genes are contributed by the ovule parent from a different population.

WL-C290 Alfalfa
Technical Description

WL-C290 is synthetic variety alfalfa derived from 115 high-yielding and persistent plants selected for resistance to silverleaf whitefly (*Bemisia argentifolii*). The WL-C290 synthetic variety alfalfa is the result of recurrent phenotypic selection for resistance to silverleaf whitefly (SLWF) carried out in a field nursery near Westmorland, Calif., U.S.A. Subsequent selection was performed for resistance (yield and survival) to silverleaf whitefly in a field trial near Westmorland, Calif. The 115 plants used as parental selections were grown in an isolation cage at Bakersfield, Calif. Breeder seed (synthetic generation 1, or "Syn 1") was bulked (all seed from all plants) following harvest in year 18 (year numbers herein are referenced to an arbitrarily chosen "year 1" of the breeding program).

Breeder seed was produced in year 18 on 115 plants using bee pollination under cage isolation at Bakersfield, Calif. One generation of Breeder seed (Syn 1), and two generations each of Foundation seed (Syn 2 or 3) and Certified seed (Syn 3 or 4) are recognized by the inventors. The maximum permitted length of stand for Foundation and Certified seed fields are 3 and 5 years, respectively. Foundation (Syn 2) seed was produced near Firebaugh, Calif. in sufficient quantity for the life of the WL-C290 variety and will be maintained by W-L Research Inc. The ATCC Designation of the seed is "WL-C290."

The primary uses of this WL-C290 variety are hay, haylage, greenchop and dehydration.

Figure 1B:
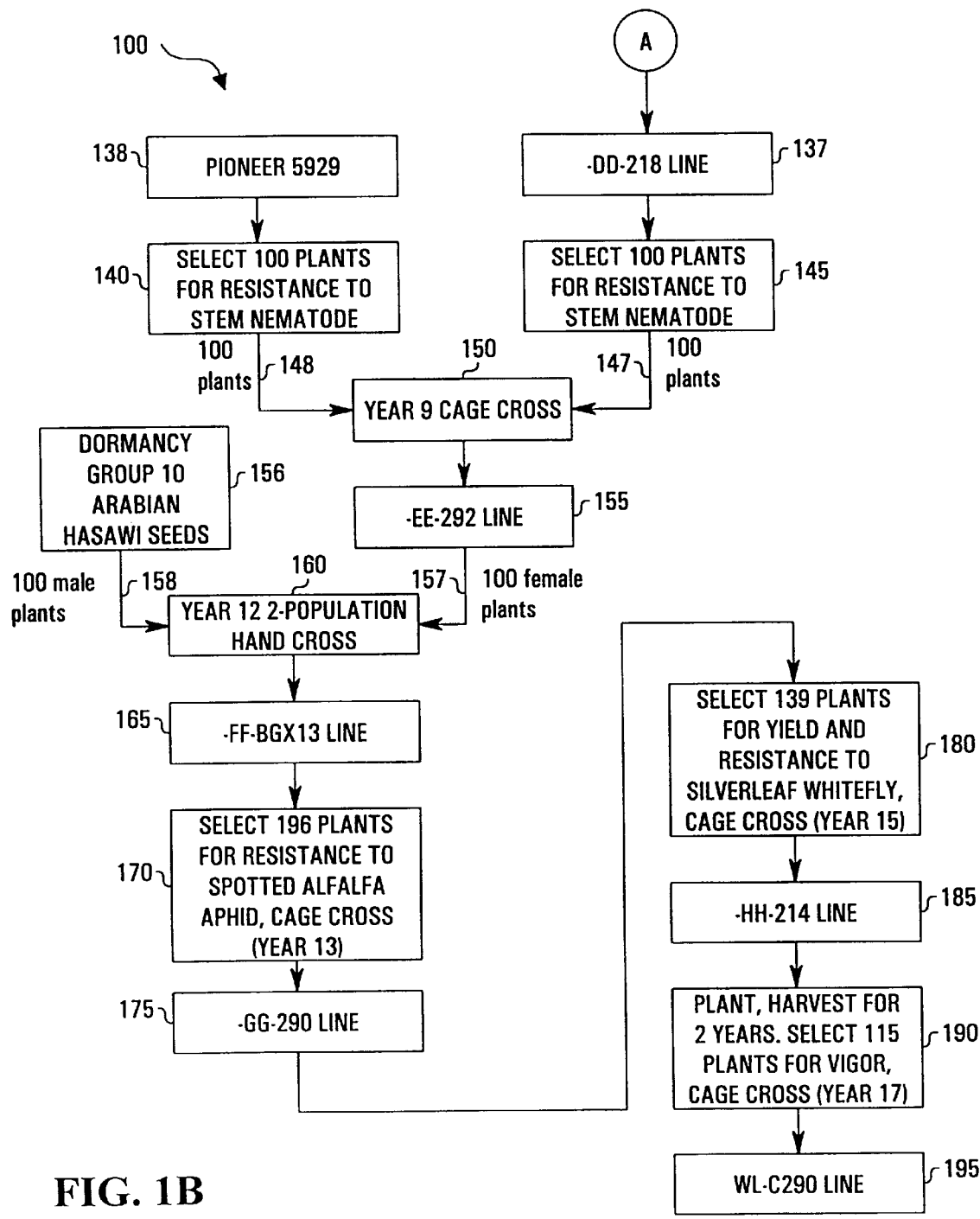

Source material for WL-C290 traces to two high-yielding, very non-dormant lines (i.e., well suited for hot-weather climates such as the Imperial Valley of Calif. in the United States, as well as areas of Mexico, Egypt, and Saudi Arabia) that were selected for resistance to spotted alfalfa aphid. Parental germplasm traces to Hasawi (a Saudi Arabian ecotype) (50%), WL 605 (25%), and Pioneer 5929 (25%), with breeding and selection steps as shown in FIG. 1 (comprising FIGS. 1A and 1B, which are described below). WL 605 alfalfa is a commercially released and available product of W-L Research Inc. The approximate germplasm source contributions for WL 605 are thought to be: Turkistan—22%, Flemish—1%, Chilean—5%, Indian—12%, and African—59%. Pioneer 5929 alfalfa is a commercially released and available product of Pioneer Hi-Bred International, Inc., Des Moines, Iowa. The approximate germplasm source contributions for Pioneer 5929, according to Pioneer are thought to be: 57 clones from CUF 101, 1 clone from MOAPA 69, and four clones of Pioneer experimental lines from Indian and African sources.

Approximate germplasm source contributions to WL-C290 are thought to be: Chilean—2%, Peruvian—3%; Indian—10%; African—30%; Turkistan—5%; and Arabian—50%.

The flower color at full bloom of WL-C290 at synthetic generation two (Syn 2) approaches 100% purple, with traces of cream and variegated. (See USDA Agriculture Handbook No. 424—A System for Visually Classifying Alfalfa Flower Color.) At full bloom, WL-C290 is approximately 100% purple, trace cream, 0% yellow, trace variegated, 0% white.

The fall dormancy class that WL-C290 is most similar to is Fall Dormancy Class 10 (FD 10). No Group 10 check variety is currently recognized; a standard test is under development by Dr. Larry Teuber at the University of California at Davis. However, in all comparisons WL-C290 is significantly taller (less dormant) than the Group 9 check variety CUF 101. Hasawi is widely recognized as a highly winter-active germplasm with fall growth characteristics significantly different than CUF 101. WL-C290 produces fall dormancy ratings nearly identical to Hasawi. The fall dormancy reaction of WL-C290 is characterized as a Dormancy Group 10. The winter activity of WL-C290 is significantly greater than CUF 101.

WL-C290 is thus adapted for use in the southwestern United States and other regions having similar climates or regions where very non-dormant alfalfas are grown, such as Mexico, Argentina, and Saudi Arabia. WL-C290 has been yield tested in California.

WL-C290 has high resistance to fusarium wilt, blue alfalfa aphid, pea aphid, northern root knot nematode, and southern root knot nematode; and resistance to phytophthora root rot, spotted alfalfa aphid, stem nematode, and silverleaf whitefly. Reaction to anthracnose (Race 1), verticillium wilt, bacterial wilt, and Aphanomyces root rot (Race 1) has not yet been adequately tested.

Under field conditions, WL-C290 displays resistance (no stunting or yellowing, significantly reduced immature whitefly densities and honeydew stickiness) to the silverleaf whitefly when compared to competitive varieties.

WL-C290 is a persistent and high yielding variety, especially in climates favorable to Dormancy Group 10 varieties. WL-C290 is also the first alfalfa release to display resistance to the silverleaf whitefly, with excellent forage yields and reduced stickiness even under heavy whitefly infestations.

Pedigree and Method used to Create WL-C290

FIG. 1A and FIG. 1B together form FIG. 1, which shows a schematic representation of the breeding and selecting process (method 100) for one embodiment of the present invention having a goal of producing a Dormancy Group 10 alfalfa that is resistant to silverleaf whitefly.

The family line from which WL-C290 was derived originated from a two-population cross (step 160 of FIG. 1B) of 100 plants (germplasm plants 158) from the land variety (an ecotype) "Hasawi" with 100 plants (germplasm plants 157) of a W-L Research Inc. experimental line -EE-292 by hand in a greenhouse environment in Bakersfield, Calif. in year 12. The Hasawi was used as the pollen (male) parent only (germplasm plants 158). The Hasawi variety (germplasm seeds 156) was collected by Asgrow Seeds, Inc. from Saudi Arabia in year 7. The -EE-292, used as the ovule (female) parent only (germplasm plants 157), originated from a year 9 cage cross (step 150) of 100 surviving plants of Pioneer 5929 (germplasm plants 138), screened for resistance to stem nematode (step 140), with 100 surviving plants (germplasm plants 147) of W-L Research Inc. experimental line -DD-218 screened for resistance to stem nematode (step 145). The -DD-218 line (germplasm plants 137) resulted from a cage cross of 177 plants selected for resistance to anthracnose (step 136 of FIG. 1A) from an -CC-CaA line (germplasm plants 135). The -CC-CaA line (germplasm plants 135) resulted from a cage cross of 130 plants selected for resistance to stem nematode (step 134) from the WL 605 line (germplasm plants 133), a line that was commercialized and available from W-L Research Inc. The WL 605 (germplasm plants 133) line resulted from a cage cross of 191 plants selected for resistance to phytophthora root rot (step 132) from a CA-BB-40 line (germplasm plants 131). The CA-BB-40 line (germplasm plants 131) resulted from a year 5 cage cross (step 130) of 50 plants (germplasm plants 128) of an old W-L Research Inc. experimental line CA-AA-86 (germplasm seeds 115), derived from selection of Dormancy Group 9 plants for high resistance to the blue alfalfa aphid (step 110) from CUF 101, Siriver, UC 123, and UC 143 (germplasm plants 108), with 50 plants (germplasm plants 127) of A77-10B (germplasm seeds 125), an experimental line from the University of California, Riverside selected out of Arabian germplasm (germplasm plants 107) for high resistance to phytophthora root rot (step 120) in year 0. CUF 101 is a publicly released alfalfa variety from the United States Department of Agriculture (USDA). Siriver is a publicly released alfalfa variety from Australia. UC 123 and UC 143 are publicly released alfalfa germplasms from the University of California.

The first resultant population of the WL-C290 family line from the original cross (step 160 of FIG. 1B) of Hasawi with -EE-292 was -FF-BGX13 (germplasm seeds 165). Plants from this population were subsequently screened for resistance to the spotted alfalfa aphid in year 13 (step 170) and the most resistant 196 plants crossed in cage at Bakersfield, Calif. to produce the population -GG-290 (germplasm seeds 175). This population was planted in a field yield trial near El Centro, Calif. in year 14 and harvested for one year. During that year (year 14), whitefly infestation was the worst ever recorded at El Centro. Most entries in the trial were severely injured with significant loss of stand. However, -GG-290 experienced visibly less injury and stand loss, so 139 vigorous surviving plants were dug in the fall of year 14 and put into a cage cross at Bakersfield, Calif. in year 15 (step 180) to produce the population -HH-214 (germplasm seeds 185). This population was then planted in a field yield trial near Westmorland, Calif. in the fall of year 15 and harvested for two years (step 190). Whitefly infestations occurred during both years of the trial, but at levels less than that of year 14. In the fall of year 17, the most vigorous 115 surviving plants of -HH-214 were selected from the yield trial and crossed in cage at Bakersfield, Calif. in year 18 (again step 190) to produce the population WL-C290 (germplasm seeds 195).

In one embodiment, the present invention comprises seeds produced from a cage cross or other conventional breeding technique that includes SLWF-resistant plants generated using at least a portion of the method shown in FIGS. 1A and 1B and described above. In another embodiment, the present invention comprises tissue culture and/or plants produced by such tissue culture, wherein the tissue culture is derived, in whole or in part, from a regenerable plant part, selected from the group consisting of leaves, roots, root tips, root hairs, anthers, pistils, stamens, pollen, ovules, flowers, seeds, embryos, stems, buds, cotyledons, hypocotyls, cells and protoplasts of the SLWF-resistant plants generated using at least a portion of the method shown in FIG. 1A and 1B and described above. Basic tissue-culture techniques and methods suitable for producing and growing such tissue culture are well known in the art. Some exemplary methods for tissue culture and regeneration of alfalfa plants from tissue culture are described in U.S. Pat. No. 5,324,646 issued Jun. 28, 1994, which is hereby incorporated by reference. It is also obvious that such tissue culture could, but need not, involve the introduction of foreign DNA into the alfalfa germplasm of the present invention.

Pest-resistance and Yield Characteristics

Pest-resistance tests were conducted by standard procedures and scoring systems as described in the NAAIC *Standard Tests to Characterize Alfalfa Cultivars*, 3rd Edition, as amended, 1995.

FIG. 2, comprising the tables shown in FIGS. 2A–2K, shows results of pest-resistance tests on the WL-C290 variety (called the "test variety") and various check varieties. The least significant differences (LSD) in FIG. 2 and elsewhere in this description (unless otherwise noted) are with respect to the protected LSD test, using an F-test followed by a one-tailed t-test of statistical significance. FIG. 2A is a table comparing the test variety WL-C290 to other alfalfa varieties for resistance to fusarium wilt. FIG. 2B is a table comparing the test variety WL-C290 to other alfalfa varieties for resistance to phytophthora root rot. FIG. 2C is a table comparing the test variety WL-C290 to other alfalfa varieties for resistance to stem nematode. FIG. 2D is a table comparing the test variety WL-C290 to other alfalfa varieties for resistance to pea aphid. FIG. 2E is a table comparing the test variety WL-C290 to other alfalfa varieties for resistance to spotted alfalfa aphid. FIG. 2F is a table comparing the test variety WL-C290 to other alfalfa varieties for resistance to blue alfalfa aphid. FIG. 2G is a table comparing the test variety WL-C290 to other alfalfa varieties for resistance to northern root knot nematode. FIG. 2H is a table comparing the test variety WL-C290 to other alfalfa varieties for resistance to southern root knot nematode. FIG. 2I is a table comparing the test variety WL-C290 to other alfalfa varieties for resistance to silverleaf whitefly. FIG. 2J is a table comparing the test variety WL-C290 to other alfalfa varieties for resistance to bacterial wilt. FIG. 2K is a table comparing the test variety WL-C290 to other alfalfa varieties for resistance to anthracnose.

FIG. 3A is a table comparing the test variety WL-C290 to other alfalfa varieties for yield in the Westmorland, Calif. area in year 19. In this comparison test, the alfalfa from each variety was harvested on July 21, August 23, September 23, and October 24 of year 19. The WL-C290 variety (also called B-147) provided the highest overall yield measured in tons of air-dry hay per acre (109% of the check variety yield) in this comparison, while Hasawi (one parental germplasm source for WL-C290) had the lowest yield (86% of the check variety yield). The other variety entries listed in FIG. 3A include the publicly available varieties Cibola, CUF 101, WL 525HQ (available from W-L Research Inc.), Mecca II (available from P.G.S. Seeds, Des Moines, Iowa.), Coronado (available from Novartis Seeds, Minneapolis, Minn.), WL 612 (also available from W-L Research Inc.), Pioneer 5939 (called PIO 5939, and available from Pioneer Hi-Bred International, Inc., Des Moines, Iowa), Kern (available from Novartis Seeds, Minneapolis, Minn.), and Hasawi. Those varieties labeled B-nnn (such as B-293) are experimental lines of W-L Research Inc.

FIG. 3B is a table comparing the test variety WL-C290 to other alfalfa varieties for yield in the Bakersfield, Calif. area in year 19. In this comparison test, the alfalfa from each variety was harvested on April 28, May 28, June 25, October 2, and November 13 of year 19. The WL-C290 variety (also called B-147) provided the highest overall yield measured in tons of air-dry hay per acre (107% of the check variety yield) in this comparison. The other variety entries listed in FIG. 3B include the publicly available varieties Mecca II, Coronado, Pioneer 5939 (called PIO 5939, and available from Pioneer Hi-Bred International, Inc., Des Moines, Iowa), WL 525HQ (available from W-L Research Inc.), Corona (available from Simplot Seeds, Fresno, Calif.), WL 612 (also available from W-L Research Inc.), Maricopa, Condor, and Kern. Those varieties labeled B-nnn (such as B-293) are experimental lines of W-L Research Inc.

Table 1 below compares the growth height of WL-C290 and three comparison varieties in October and November of year 19, in Bakersfield and Westmorland, Calif.-area tests. The WL-C290 variety is clearly the tallest in these comparisons.

TABLE 1

Fall Dormancy/Winter Activity Reaction*

| Test Location | Date Last Cut (Mo/Yr) | Date Measured Mo/Yr) | Average Height Inches | | | | CV |
|---|---|---|---|---|---|---|---|
| | | | WL-C290 | Moapa 69 | CUF 101 | Mecca II | LSD .05** | % |
| Bakersfield, CA | 10/19 | 11/19 | 18.3 | 13.0 | 14.4 | 14.8 | 1.3 | 9.6 |
| Westmorland, CA | 10/19 | 11/19 | 18.0 | 14.5 | 16.5 | 16.6 | 1.4 | 10.0 |

*The NAVRB (National Alfalfa Variety Review Board) does not currently recognize a Dormancy Group 10 check variety; Dr. Larry Teuber (UC-Davis) plans to provide a very non-dormant check variety by 1998. However, at the 1996 year's meeting the Review Board did state that any variety significantly (5% level) taller (less dormant) than CUF 101 (current Dormancy Group 9 check variety) would be given a Dormancy Group 10 fall dormancy rating by the NAVRB.Therefore, WL-C290 falls into a Dormancy Group 10 classification for fall dormancy reaction.
**The LSD values are with respect to the protected least significant differences (LSD) test, with LSD values calculated from a one-tailed t-test.

Figure 4A:
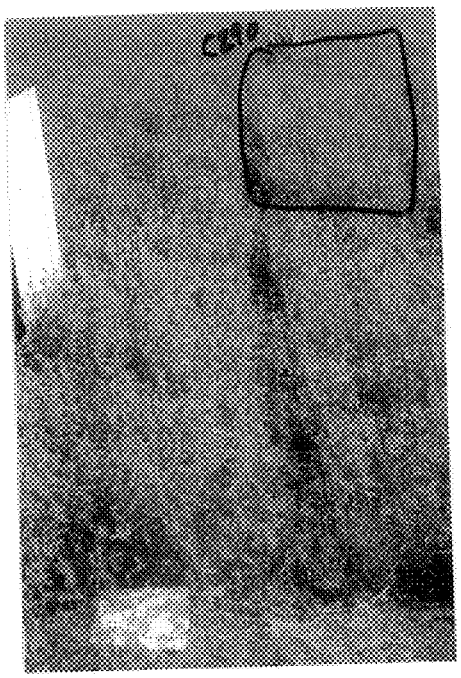
FIG. 4A is a photograph taken August 29 of year 20 showing a stand of CUF 101 on the left and WL-C290 in the upper right, after heavy whitefly pressure.
Figure 4B:
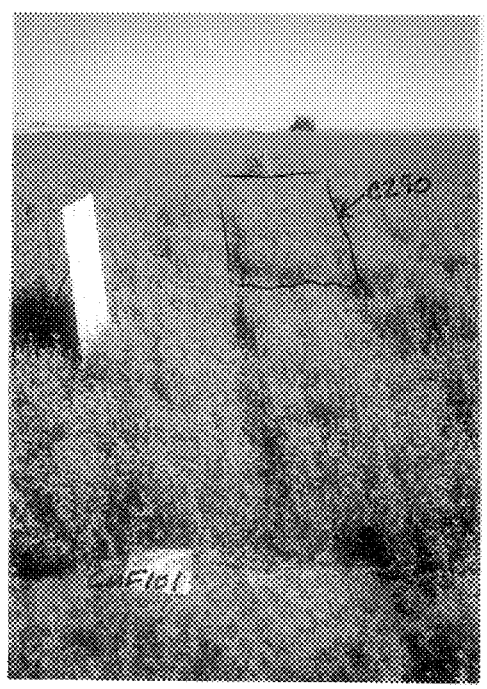
FIG. 4B is a photograph taken August 29 of year 20 showing a stand of CUF 101 on the middle left and of WL-C290 in the upper middle right showing height advantage and darker green color, after heavy whitefly pressure.
Figure 4C:
FIG. 4C is a photograph taken August 29 of year 20 showing a stand of WL-C290 in front of the board showing height advantage and darker green color, after heavy whitefly pressure.
Figure 4D:
FIG. 4D is a photograph taken August 29 of year 20 showing a stand of CUF 101 on the left and of WL-C290 in the middle behind the clipboard, after heavy whitefly pressure.

FIG. 4A is a photograph taken August 29 of year 20 showing a stand of CUF 101 on the left and WL-C290 in the upper right, after heavy whitefly pressure. FIG. 4B is a photograph taken August 29 of year 20 showing a stand of CUF 101 on the middle left and WL-C290 in the upper middle right showing height advantage and darker green color, after heavy whitefly pressure. FIG. 4C is a photograph taken August 29 of year 20 showing a stand WL-C290 in front of the board showing height advantage and darker green color, after heavy whitefly pressure. FIG. 4D is a photograph taken August 29 of year 20 showing a stand of CUF 101 on the left and WL-C290 in the middle behind the clipboard, after heavy whitefly pressure, showing dramatic evidence of SLWF resistance, and resultant superior persistence, color, and height. The photographs of FIGS. 4A–4D were taken in the Westmorland, Calif. area.

Figure 5:
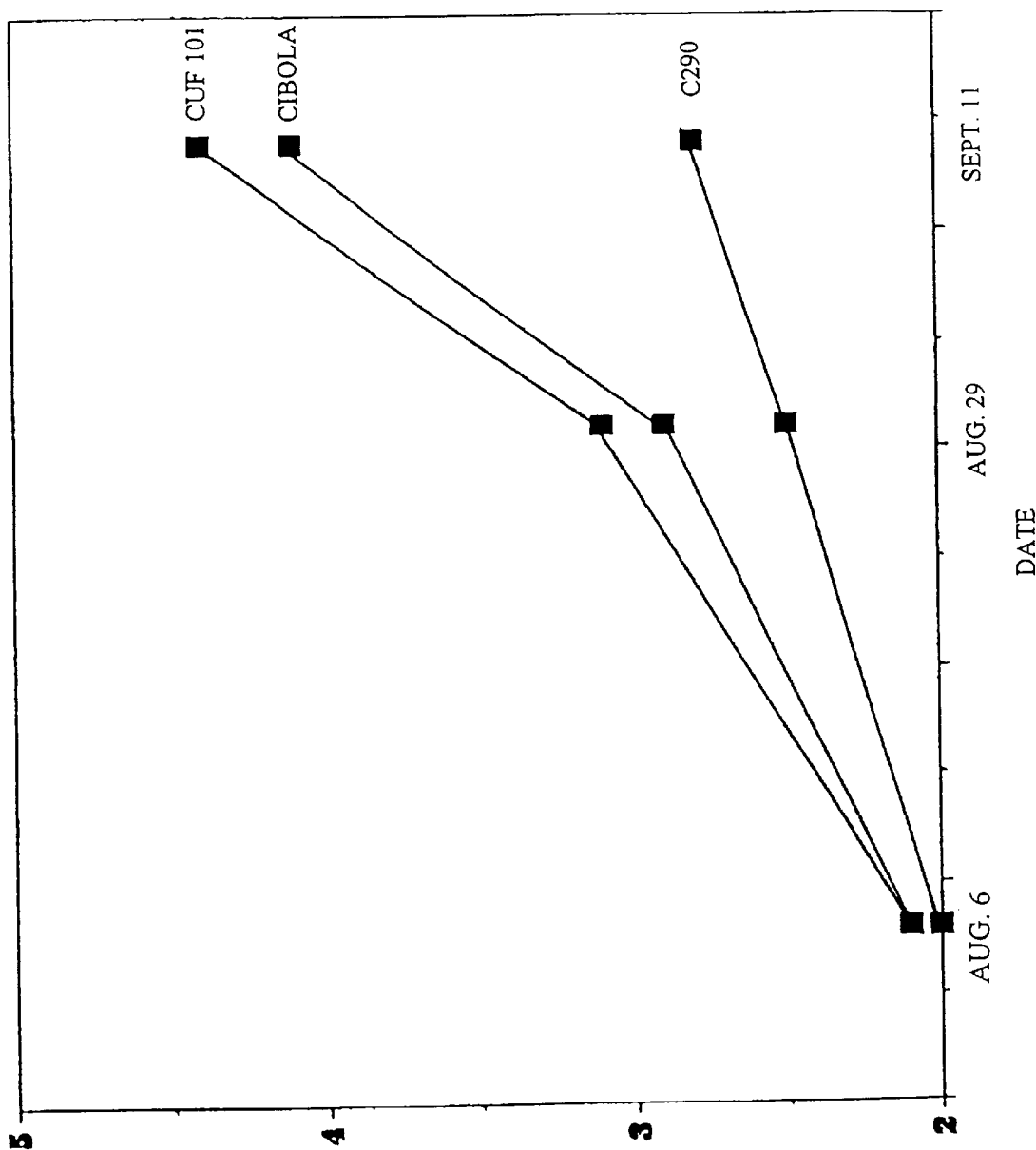
FIG. 5 shows a graphical representation of comparisons of SLWF resistance of WL-C290 versus CUF 101 and CIBOLA, as demonstrated over time in year 20.

Tables 2, 3, and 4 below show comparisons of SLWF resistance as demonstrated over time (three measurements made in year 20 of a stand planted in Westmorland, Calif. in year 18). FIG. 5 shows a graphical representation of these data. It is clear that as whitefly infestation became more severe (i.e., later in the year as there are more whiteflies), the resistance of WL-C290 relative to varieties Cibola and CUF 101 (which are possible check varieties) became much more pronounced. (CUF 101 is a non-dormant, blue-aphid-resistant public variety often used as a standard to which new germplasm is compared.) The September of year 20 evaluation (Table 4) showed WL-C290 to be statistically significantly greater in resistance to SLWF than were the comparison varieties.

TABLE 2

Westmorland, California
Year 20 Variety Evaluation - Silverleaf Whitefly Resistance
Planted: November 2, year 18; Scored: August 6, year 20
4 Replicates

| Entry | A.S.I. | % Resist. |
|---|---|---|
| 1. WL-C290 | 2.0 | 96.0 |
| 2. CIBOLA | 2.1 | 71.9 |
| 3. CUF 101 | 2.1 | 86.7 |
| MEAN | 2.07 | 84.88 |
| LSD @ .05 | 0.31 | 12.71 |
| LSD @ .01 | 0.41 | 16.90 |
| CV % (coefficient of variation) | 10.59 | 10.59 |

A.S.I. Score: 1 = near immune; 3 = moderate resistance; 5 = high susceptibility
A.S.I. = Average Seventy Index, wherein growing plants are dug up and placed in classification piles after inspection. One takes the number of plants in each pile and generate a weighted index. 0 is a completely healthy plant; 5 is a dead plant.

TABLE 3

Westmorland, California
Year 20 Variety Evaluation - Silverleaf Whitefly Resistance
Planted: November 2, year 18; Scored: August 29, year 20
4 Replicates

| Entry | A.S.I. | % Resist. |
|---|---|---|
| 1. WL-C290 | 2.8 | 42.5 |
| 2. CIBOLA | 2.9 | 34.6 |
| 3. CUF 101 | 3.1 | 19.9 |
| MEAN | 2.84 | 34.77 |
| LSD @ .05 | 0.50 | 29.03 |
| LSD @ .01 | 0.67 | 38.61 |
| CV % | 12.55 | 59.03 |

A.S.I. Score: 1 = near immune; 3 = moderate resistance; 5 = high susceptibility

TABLE 4

Westmorland, California
Year 20 Variety Evaluation Silverleaf Whitefly Resistance
Planted: November 2, year 18; Scored: September 11, year 20
4 Replicates

| Entry | A.S.I. | % Resist. |
|---|---|---|
| 1. WL-C290 | 2.8 | 42.5 |
| 2. CIBOLA | 4.1 | 1.4 |
| 3. CUF 101 | 4.4 | 0.0 |
| MEAN | 3.80 | 14.62 |
| LSD @ .05 | 0.34 | 16.47 |
| LSD @ .01 | 0.45 | 21.90 |
| CV % | 6.28 | 79.62 |

A.S.I. Score: 1 = near immune; 3 = moderate resistance; 5 = high susceptibility

Additional Pest-resistance and Yield Tests

Additional tests were conducted by and/or for W-L Research, Inc. in test plots located in the Imperial Valley of California and elsewhere. Tables 5, 6, and 7 show the results of these tests. Tables 5 and 6 show summary comparisons of pest resistance, comparing WL-C290 to various resistant check varieties (varieties accepted by the NAVRB as resistant to a particular pest or disease) and various susceptible check varieties (varieties accepted by the NAVRB as susceptible to a particular pest or disease). Table 7 shows agronomic performance with respect to yield (tons per acre).

TABLE 5

WL-C290 Pest Resistance Summary

| | % Resistance | | | |
|---|---|---|---|---|
| Pest | WL-C290 | Resistant Check | Susceptible Check | NAVRB Rating |
| Fusarium wilt | 58 | 54 | 7 | HR |
| Phytophthora root rot | 35 | 46 | 0 | R |
| Blue alfalfa aphid | 56 | 55 | 5 | HR |
| Pea aphid | 60 | 55 | 4 | HR |
| Spotted alfalfa aphid | 36 | 60 | 0 | R |
| Stem nematode | 37 | 32 | 1 | R |
| Southern Root knot nematode | 55 | 50 | 1 | HR |
| Northern Root knot nematode | 56 | 90 | 7 | HR |
| Anthracnose | 0 | 65 | 1 | S |
| Bacterial wilt | 5 | 42 | 0 | S |

(NAVRB = National Alfalfa Variety Review Board; HR = high resistance, R = resistant, MR = moderate resistance, LR = low resistance, S = susceptible)

TABLE 6

Pest Resistance Head-to-Head Comparisons

| Variety | Fall Dorm. | Blue Aphid | Pea Aphid | Spotted alfalfa Aphid | Fusarium Wilt | Phytophthora Root Rot | Bacterial Wilt | Verticillium Wilt | Anthracnose | Stem Nematode | S. Root Knot Nematode | N. Root Knot Nematode |
|---|---|---|---|---|---|---|---|---|---|---|---|---|
| WL-C290 | 10 | HR | HR | R | HR | R | S | —* | S | R | HR | HR |
| Condor | 8 | HR | HR | HR | HR | HR | — | — | — | MR | HR | LR |
| DK 189 | 8 | R | R | HR | HR | R | MR | MR | HR | MR | R | — |
| Kern | 8 | HR | HR | HR | HR | HR | MR | MR | HR | R | HR | — |

TABLE 6-continued

Pest Resistance Head-to-Head Comparisons

| Variety | Fall Dorm. | Blue Aphid | Pea Aphid | Spotted alfalfa Aphid | Fusarium Wilt | Phytophthora Root Rot | Bacterial Wilt | Verticillium Wilt | Anthracnose | Stem Nematode | S. Root Knot Nematode | N. Root Knot Nematode |
|---|---|---|---|---|---|---|---|---|---|---|---|---|
| Maricopa | 8 | R | HR | HR | HR | R | MR | MR | LR | R | HR | LR |
| Pioneer 5715 | 8 | HR | HR | HR | HR | R | LR | LR | HR | — | — | — |
| Pioneer 5888 | 8 | R | R | HR | HR | R | — | — | — | R | — | — |
| WL 525 HQ | 8 | HR | HR | HR | HR | HR | MR | — | — | R | HR | MR |
| Coronado | 9 | HR | HR | HR | HR | R | S | MR | R | R | HR | MR |
| CUF 101 | 9 | HR | HR | HR | — | — | — | — | — | — | MR | — |
| Meccall | 9 | HR | HR | HR | HR | R | LR | LR | LR | R | — | — |
| Pioneer 5939 | 9 | R | R | HR | HR | HR | LR | LR | R | R | — | — |
| SW14 | 9 | R | HR | HR | HR | LR | — | LR | — | — | MR | — |
| WL 612 | 9 | HR | HR | HR | HR | HR | — | — | LR | HR | MR | MR |

*WL-C290 Reaction to Verticillium wilt has not yet been tested.

TABLE 7

Head-to-Head Yield Comparisons

| Variety X | WL-C290 Yield as % of Variety X | Yield WL-C290 tons/acre | Yield Variety X | No. of Tests | # Cuts |
|---|---|---|---|---|---|
| Baralfa 85 | 106 | 8.16 | 7.70 | 2 | 10 |
| Condor | 108 | 9.32 | 8.66 | 1 | 5 |
| Corona | 107 | 9.32 | 8.69 | 1 | 5 |
| Coronado | 106 | 8.16 | 7.67 | 2 | 10 |
| CUF 101 | 106 | 6.99 | 6.58 | 1 | 5 |
| DK189 | 108 | 9.32 | 8.60 | 1 | 5 |
| Hasawi | 127 | 6.99 | 5.49 | 1 | 5 |
| Kern | 113 | 8.16 | 7.21 | 2 | 10 |
| Maricopa | 110 | 9.32 | 8.49 | 1 | 5 |
| Mecca II | 105 | 8.16 | 7.74 | 2 | 10 |
| Pioneer 5939 | 108 | 8.16 | 7.59 | 2 | 10 |
| UC Cibola | 105 | 6.99 | 6.64 | 1 | 5 |
| WL 457 | 115 | 9.32 | 8.11 | 1 | 5 |
| WL 525 HQ | 108 | 8.16 | 7.59 | 2 | 10 |
| WL 612 | 109 | 8.16 | 7.51 | 2 | 10 |
| 13R Supreme | 121 | 9.32 | 7.71 | 1 | 5 |

The Economic Impact of Silverleaf Whitefly

Agriculture in the southwestern United States has come under attack by many different types of "flies," including Medflies, Mexflies, and cotton whiteflies. But none can hold a candle to the damage wrought by the tiny insect silverleaf whitefly. Originally referred to as the poinsettia whitefly (much to the dismay of the ornamental plant industry), growers now call it "superbug."

Damage to U.S. crops from silverleaf whitefly (Bemisia argentifolii, Bellow and Perring) was estimated at $200 million in 1991 and $500 million in 1992. The silverleaf whitefly (SLWF) was formerly known as "strain B" of the sweetpotato whitefly (SPWF-B), (Bemisia tabaci, Gennadius). University of California, Riverside scientists have identified this whitefly as a distinct species from the sweetpotato whitefly (Bemisia tabaci) and have named it the silverleaf whitefly (Bemisia argentifolii). The name comes from the insect's ability to cause squash silverleaf, a silvering symptom on squash plants that results from SLWF feeding. The silverleaf whitefly (SLWF) is present in both the Low Desert (a geographic production area including the Coachella, Imperial, and Palo Verde valleys) and the Central Valley of Califorina and threatens California agriculture and horticulture statewide. The SLWF is a devastating agricultural pest in California's Low Desert alfalfa production region. In Imperial County, alfalfa ranks second in gross agricultural earnings and occupies approximately one-third of all agricultural acreage. From the fall of 1991 to April 1994, crop damage caused by the SLWF totaled $336 million in Imperial County alone, and losses to Imperial County alfalfa producers were estimated to exceed $26 million per year.

The silverleaf whitefly is more damaging and, unfortunately, more difficult to control than other whitefly species. Factors contributing to the severity of damage are the SLWF's higher reproductive rate compared with other whitefly species, much wider host range, greater production of sticky honeydew exudate and its association with phytotoxic disorders in some plant species. Populations of this relatively new agricultural pest have demonstrated an astounding capacity to develop resistance to insecticides, an important consideration for plant breeders. In addition, there are no highly effective natural enemies of the SLWF.

Initially SLWF was a problem for human food crops such as melons. In heavily irrigated areas such as the Imperial Valley of Calif., it becomes important to rotate crops, both in order to restore nutrients to the soil, as well as to prevent undue accumulation of pests (by planting a crop which is unsuitable as a host for a particular pest, the number of surviving pests and pest eggs declines over time). At that time, the fact that SLWF could be a major damaging factor in alfalfa as a crop was not yet known. The inventors of the present invention recognized that it would be important to have alfalfa as such a rotation crop, and that is important to develop a variety of alfalfa that was both suited to a hot climate and long growing season, and particularly resistant to SLWF.

There are no controlled experiments that clearly quantify SLWF damage to alfalfa in terms of yield or forage quality reduction. This is partly due to the inability to create an uninfested control. Grower records, Imperial Country Agricultural Commissioner annual reports and UC forage-yield-trial records all strongly suggest, however, that the SLWF may directly or indirectly reduce alfalfa forage yield by 10 to 25%. Imperial County Agricultural Commissioner's reports since 1990 show a 17% reduction in annual alfalfa hay yield.

Developing Silverleaf Whitefly Resistance in Alfalfa

Outbreaks of silverleaf whitefly (SLWF) continue in the southwestern United States. Though the population numbers are not as staggering as the 1991 outbreak, the whitefly is still making its presence known.

The SLWF feeds on over 500 different plants, including cotton, alfalfa, lettuce, grapes, citrus, and any and all cole crops and melons. The whitefly damages plants several ways. Whitefly adults and nymphs, also called immatures, weaken alfalfa plants by sucking the juices (A. Behling, *Hay and Forage Grower*, March 1997). SLWF is capable of sucking four to five times as much plant nutrients out of a host plant as the sweetpotato whitefly and subsequently, it produces four to five times as much honeydew. Honeydew, a sticky sugary substance secreted by both whiteflies and aphids, covers the leaves and supports the growth of a black fungus called sooty mold. This further reduces any value the surviving crop may have because sticky alfalfa is difficult to cut and bale, and sooty alfalfa has poor feed quality. It also gives hay a grayish look that resembles rain damage, making it unmarketable in some cases. Besides alfalfa—grown on 51% of the Imperial Valley's 500,000 acres—whiteflies have destroyed cotton, melon, and vegetable fields.

The first record of the sweetpotato whitefly in the United States was from Florida in 1894. Almost a century later (1986), Florida poinsettia growers experienced devastating outbreaks of sweetpotato whitefly. Chemicals were ineffectual in controlling the outbreak. Whiteflies are not really flies, but are closely related to the aphids, leafhoppers and scale insects. Whiteflies differ from aphids in having fine, long and short white waxy threads radiating from their body and wings, giving them the appearance of having been dusted with a fine white material.

Understanding the life history of the SLWF can help in developing control methods. Developmental threshold temperatures start at 50° F., with the upper level near 90° F. Developmental time varies seasonally with the transition from egg to adult taking from 25 to 50 days. Adult females live from 10 to 15 days during the summer months and may live several months during the winter. Fertility can vary from 80 to 300 eggs per female. The SLWF develops and breeds continuously as long as temperature conditions permit. Female SLWF prefer to lay their eggs on young foliage and the newly hatched crawlers do not move any significant distance from the hatching site. High reproductive rates and a large range of host plants provide excellent conditions for population growth.

The new whitefly strain, the silverleaf whitefly (SLWF), is about 30% more efficient at reproduction. When temperatures are about 90° F., a generation can be produced in about 18 days. Each female can lay as many as 300 eggs, of which two-thirds may be female. In theory, one female may produce 200 females, which produce 40,000 females, which subsequently may produce 8,000,000 females in just three generations (approximately 54 days during the warmer seasons). During the height of the outbreak, plants in the Imperial Valley of Calif. were covered with SLWF at an estimated population level of 3000 whiteflies per square inch. At this level of infestation, plant mortality was common.

University of California, Riverside entomologist Thomas Perring and his associates developed sampling techniques to determine host plant preference ratings for crops and weeds. Whitefly population surveys were conducted by Perring on 35 weeds and 15 crop species. An interesting revelation from the survey was that alfalfa, while a host plant of SLWF, is not a primary host. Alfalfa does harbor whiteflies. Adults and nymphs are found on it. Because of the seriousness of the SLWF problem, there is a need to develop an alfalfa that is less attractive to SLWF.

In the fall of one year, W-L Research Inc.'s test plots of alfalfa in Imperial Valley, Calif. were devastated by SLWF. One entry, originally selected from Middle-Eastern germplasms for its very non-dormant growth characteristics, exhibited slightly less damage and rapid recovery from SLWF feeding. Selected parent plants from this entry were dug and intercrossed inside an isolation cage. Seed from this first cycle of selection was planted in the Imperial area. Over two years it was reselected for SLWF damage, yield and persistence. Natural epidemics can be utilized to select plants with resistance. Historically, outbreaks have been particularly useful for isolating plants resistant to pea and spotted alfalfa aphid.

Two cycles of field selection have resulted in a germplasm, WL-C290, that seems to exhibit far less SLWF damage, greater yields and better persistence than either unselected lines or other commercially available varieties. Primary selection criteria are SLWF nymph density on plant surfaces, and plant yield. Plant stickiness due to honeydew secretions was found to be more difficult to measure consistently. Additional information and possible additional selections for improved performance will provide improved performance, yield, and SLWF-resistance level.

Insecticides have been ineffectual in controlling the SLWF pest for several reasons. Researchers at the University of California, Riverside reported that whiteflies are sensitive to permethrin insecticides, but only the early stages of whitefly were highly sensitive to the compounds. Secondly, with most pesticides applied by air and with the whitefly residing on the underside of leaves, the likelihood of good target coverage is remote. In addition, any field that is treated is quickly overwhelmed by whiteflies moving in from surrounding fields. Modified application techniques involving high-pressure, high-volume applications show some promise, but logistical problems are common and limit the use of this technology.

Potential biological control agents of SLWF include pathogens, parasites and predators. Efforts are already underway to evaluate and release currently available North American predators and parasites. Known entomopathogenic (insect-killing) fungi are also being scrutinized for effectiveness against the whitefly. Additional natural enemies may be imported if USDA and University studies show them to be effective against the SLWF while also demonstrating safety to native non-pest species.

On the plant resistance front, W-L Research Inc. has begun work on the incorporation of SLWF "resistance" into its experimental breeding lines of alfalfa. From test plots and nurseries located in the Imperial Valley, various breeding lines and varieties have been evaluated for their performance under heavy SLWF infestation. Table 8 shows the results from readings of percent plant survival. The data presented are preliminary, but may suggest that genetic variation exists within current non-dormant alfalfa germplasms that could allow for the development of SLWF tolerance or resistance.

TABLE 8

Imperial Valley, California Sweetpotato Whitefly Field Evaluation

| Variety | Percent Survivors |
|---|---|
| WL516 | 50 |
| CUF 101 | 49 |
| Pioneer 5929 | 46 |
| WL 610 | 38 |
| WL 605 | 26 |
| Sundor | 26 |
| Mecca | 24 |
| Mean | 37 |
| LSD (.05) | 14 |
| CV % | 25 |

The search for plant resistance should be an integral part of the whitefly control program. Although plant resistance work is often difficult and time consuming, it is an important adjunct to any integrated pest control program. The development of plant resistance to whitefly will offer several critical advantages. Alfalfa is often of lower economic value than surrounding crops, making pesticide applications to alfalfa uneconomical. By breeding an alfalfa variety with less attractiveness as a host to the pest, whitefly population levels should decrease within the alfalfa crop and chemical controls can be reduced or eliminated. As a result, natural and enhanced populations of whitefly predators and parasites will find a healthy refuge within these "resistant" alfalfa stands.

Summary Highlights Concerning the WL-C290 Invention

From test data collected by W-L Research, Inc., summary highlights concerning the WL-C290 invention are as follows:

Pest Resistance—Highlights

Resistance to the silverleaf whitefly (reduced immature whitefly densities and reduced honeydew stickiness); excellent persistence and high yield under severe whitefly infestations.

High resistance to fusarium wilt, the blue alfalfa aphid and pea aphid insures high productivity and broad, world-wide adaptation.

Resistance to Phytophthora root rot produces excellent stand establishment and maximum profitability on poorly drained and/or over-irrigated soils.

Resistance to stem nematode and high resistance to both northern and southern root knot nematodes significantly increases persistence and overall productivity on nematode-infested soils.

Fall Dormancy/Winter Activity—Highlights

Winter activity of WL-C290 is significantly greater than CUF 101; WL-C290 is a true Dormancy Group 10 variety.

Very fast recovery after harvest and excellent standability under sprinkler irrigation.

WL-C290 is an excellent companion variety to Group 9 varieties; WL-C290 can be cut 5–7 days before Group 8 varieties to spread out harvest on larger haying operations.

Forage Yield—Highlights

Excellent winning percentage in head-to-head comparisons with the latest competitive non-dormant and very non-dormant varieties.

Very high yield potential in both the San Joaquin and Imperial Valleys of Calif.

Outstanding yield potential under silverleaf whitefly infestations.

Product Differentiation

WL-C290 possesses several unique characteristics that demonstrate true product differentiation:

widely adapted and very high yielding in head-to-head comparisons with the latest competitive products;

a "true" Dormancy Group 10 variety with winter activity significantly greater than CUF 101;

resistance to the silverleaf whitefly, with reduced nymphal densities and reduced honeydew stickiness under severe whitefly infestations;

high resistance to two primary aphids (blue alfalfa and pea) and resistance to spotted alfalfa aphid provides broad, world-wide adaptation;

resistance to Phytophthora root rot insures excellent stand establishment and tolerance to over-irrigation on heavy, poorly drained soils; and very fast recovery after cutting and erect growth habit provides excellent standability under sprinkler irrigation.

In one embodiment, the present invention includes a breeding method that includes genetic material derived, in whole or in part, from alfalfa variety designated WL-C290 and having ATCC Accession No. 209502. In one such embodiment, the breeding method uses a cage-cross breeding program, in which at least some of the parent alfalfa plants include genetic material derived from alfalfa variety designated WL-C290 and having ATCC Accession No. 209502. In another such embodiment, hand cross breeding is used in which at least some of the parent alfalfa plants include genetic material derived from alfalfa variety designated WL-C290 and having ATCC Accession No. 209502. In yet another such embodiment, tissue-culture breeding is used in which genetic material is inserted into alfa cells, and in which either the cells or at least some of the genetic material are derived, in whole or in part, from alfalfa variety designated WL-C290 and having ATCC Accession No. 209502. In one embodiment, the present invention includes seed is produced by a cage-cross breeding program as described above. In another such embodiment, the present invention includes one or more alfalfa plants or parts thereof, produced by such seed or regenerable parts of said seed.

In one embodiment, genetic material derived, in whole or in part, from alfalfa variety designated WL-C290 and having ATCC Accession No. 209502 is introduced into, merged with, or crossed with genetic material of another variety of alfalfa (in one embodiment, for example, a cage-cross is performed that crosses alfalfa plants derived from alfalfa variety designated WL-C290 with alfalfa plants of another variety). In one embodiment, plants of WL-C290 are hand-crossed with a variety resistant to anthracnose and/or bacterial wilt in order to obtain an embodiment that has the desirable characteristics of WL-C290 such as resistance to SLWF, Dormancy Group 10 winter activity, and resistance to a number of other pests as shown in FIGS. 2A–2K, as well as having the anthracnose- and bacterial-wilt-resistance characteristics of the other variety. In various embodiments, phenotypic selection or marker-assisted selection techniques are used to select among the results of said cross those individual plants or plant parts which have the desired characteristics of the parental lines.

In one embodiment, phenotypic observations and selections are performed in order to identify resulting plants that exhibit desirable traits, such as SLWF resistance or yield, of both parental germplasms.

In addition to phenotypic observations, the genotype of a plant can also be examined. In one such embodiment, marker-assisted breeding is used to identify individual ones of the resulting offspring having desired traits of both WL-C290 and of the other variety.

There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The most widely used of these laboratory techniques are Isozyme Electrophoresis and RFLPs as discussed in Lee, M., "Inbred Lines of Maize and Their Molecular Markers,"

The Maize Handbook, (Springer-Verlag, New York, Inc. 1994, at 423–432) incorporated herein by reference. Other techniques that find use in the present invention are described in U.S. Pat. No. 5,675,066 issued Oct. 7, 1997, U.S. Pat. No. 5,451,705 issued Sep. 19, 1995, and U.S. Pat. No. 5,492,547 issued Feb. 20, 1996, each incorporated herein by reference.

Phenotypic traits characteristic of the expression of the hybrid genetic complement of this invention include those that are distinguishable by electrophoretic separation of DNA sequences cleaved by various restriction endonucleases. These traits (genetic markers) are termed RFLP (restriction fragment length polymorphisms).

Restriction fragment length polymorphisms (RFLPs) are genetic differences detectable by DNA fragment lengths, typically revealed by agarose gel electrophoresis, after restriction endonuclease digestion of DNA. There are large numbers of restriction endonucleases available, characterized by their nucleotide cleavage sites and their source, e.g., the bacteria E. coli. Variations in RFLP's result from nucleotide base pair differences which alter the cleavage sites of the restriction endonucleases, yielding different sized fragments.

In one embodiment, restriction fragment length polymorphism analysis of the genetic complements of this invention is conducted by one of a number of companies, for example Linkage Genetics Inc., of Salt Lake City, Utah. This service is available to the public on a contractual basis. For this analysis, the genetic marker profile of the parental varieties or lines are determined. If these lines are essentially homozygous at all relevant loci, they should have only one allele at each locus. Consequently, the diploid genetic marker profile of the hybrid offspring of the inbred parents should be the sum of those parents, e.g., if one parent had the allele A at a particular locus, and the other parent had B, the hybrid AB is by inference.

In one embodiment, probes are prepared to the fragment sequences, these probes being complementary to the sequences thereby being capable of hybridizing to them under appropriate conditions well known to those skilled in the art. These probes are labeled with radioactive isotopes or fluorescent dyes for ease of detection. After the fragments are separated by size, they are identified by the probes. Hybridization with a unique cloned sequence permits the identification of a specific chromosomal region (locus). Because all alleles at a locus are detectable, RFLP's are co-dominant alleles, thereby satisfying a criteria for a genetic marker. They differ from some other types of markers, e.g, from isozymes, in that they reflect the primary DNA sequence, they are not products of transcription or translation. Furthermore, different RFLP profiles result from different arrays of restriction endonucleases.

Co-dominant genetic markers that delineate segments of nucleic acids characterizing the genetic complement can be listed for each variety.

An important use of genetic markers is to reconstruct ("reverse engineer") parental genetic complements of an offspring. For example, the hybrid genetic complement results from the combination of two inbred parental complements. The genetic complements of the parental lines may be determined by analyzing the RFLP and isozyme genetic profiles of the hybrid. This can be done with chromosome sorting by, for example, flow cytometry, followed by DNA isolation and probing for specific RFLP markers. Alternatively, total DNA may be isolated and probed. Marker-associated DNA may be isolated and cloned. If one parent is known, the other may be determined by inference.

The markers are inherited in co-dominant fashion and follow well-known rules of mendelian inheritance. That means if a hybrid has marker AB, and one of the parental lines has marker A (genotype AA), the other parent by inference has B. If the parent is an inbred line, it is expected to be BB, because it is essentially homozygous.

Markers are DNA sequences (often linked to genes), the phenotypic expressions of which are used to identify the presence of other genes or genetic complements which co-segregate with the markers through meiosis and appear jointly in offspring. Markers are generally co-dominant, that is, both alleles at a marker locus are readily detectable in a heterozygote. Markers which are useful in plant breeding comprise isozymes and restriction fragment length polymorphism (RFLPs).

Isozymes are forms of proteins, wherein all of the proteins of an isozyme have the same enzymatic activity, but wherein such proteins are distinguishable, for example, on starch gel electrophoresis, usually by charge and/or molecular weight.

In one embodiment, a standard set of loci is used as a reference set. Comparative analysis of these loci may be used to compare the purity of hybrid seeds, to assess the increased variability in hybrids compared to inbreds, and to determine the identity of seeds, plants, and plant parts. In this respect, an isozyme or RFLP reference set may be partially used to develop genotypic "fingerprints."

For example, in one embodiment, an RFLP analysis is performed in WL-C290 to determine identifiable RFLPs in the WL-C290 variety, and an RFLP analysis is performed on the other variety (i.e., the variety having other desirable traits) to determine identifiable RFLPs therein. Achieving marker-assisted breeding using RFLP analysis is quite difficult because of the variability of DNA sequences within an alfalfa variety or even within a very small breeding population of alfalfa, however in one embodiment, well-known techniques of RFLP analysis, EST (expressed sequence tags) analysis, and/or microsatellite analysis are used in order to determine a set of markers (i.e., DNA markers associated with desirable traits) useful in the alfalfa-breeding and selection program described below. A conventional alfalfa breeding program then combines genetic material from both parental varieties, e.g., by cage-cross or hand breeding, or by transgenic gene manipulation into cells of cotyledons or hypocotyls. RFLP or other suitable marker analysis is then performed on the resulting progeny (e.g., on the resulting seeds, cotyledons, hypocotyls, cells or other plant parts), in order to identify individual offspring in which markers (e.g., RFLPs) associated with desirable traits of each parental line are found. These individuals are then selected and used in a further breeding program, thus achieving selection for the desired traits in many fewer generations than would be needed using conventional breeding and phenotypic-selection techniques.

The references listed below are incorporated herein by reference to the extent that they supplement, explain, provide a background for, or teach methodology, techniques, and/or compositions employed herein:

Armstrong and Green, (1985). "Establishment and Maintenance of Friable, Embryogenic Maize Callus and the Involvement of L-Proline," Planta, 164:207–214.

Chu, C. C., Wang, C. C., Sun, C. S., et al. (1975). Scientia Sinica 18:659–668.

Coe, E. H., et al (1988) "The Genetics of Corn and Corn Improvement", 3rd. ed., Vol. 18, Sprague and Dudley (eds) 87:258

Duvick, D. N. (1984) "Genetic Contribution to Yield Gains of U.S. Hybrid Maize-1930–1980," Genetic Contribution to Yield Gains of Five Major Crops, pp. 15–48.

Finkle, B. J., Ulrich, J. M., Rains, W., et al. (1985). Plant Sci. 42:133–140.

Goodman, M. and Stuber, C., "Genetic Identification of Lines and Crosses Using Isoenzyme Electrophoresis," Proceedings of the Thirty-Fifth Annual Corn and Sorghum Industry Research Conferences, Chicago, 1980.

Gordon-Kamm, W. et al., (1990) "Transformation of Maize Cells and Regeneration of Fertile Transgenic Plants," The Plant Cell, V.2, 603–618.

Hauptmann, R. M., Vasil, V., Ozias-Aikins, P., et al. (1988). Plant Physiol. 86:602–606.

Klein, T. M., Kornstein, L., Sanford, J. C., et al. (1989). Plant Physiol. 91:440–444.

Murashige, T. and Skoog, F. (1962). Plant Physiol. 15:473–497.

Rhodes, C. A., Pierce, D. A., Mettler, F. J., et al. (1988). Science 240:204–207.

Roberts, Nuc. Acids Res. 10:117–144 (1982).

Troyer, A. F. (1990) "A Retrospective View of Corn Genetic Resources" Journal of Heredity, 81: 17–24

Withers, L. A., King, P. J. (1979). Plant Physiol. 64:675–678.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. Seed of synthetic alfalfa variety designated WL-C290 and having ATCC Accession No. 209502.

2. An alfalfa plant produced by the seed of claim 1 or regenerable parts of said seed.

3. Seed of the alfalfa plant of claim 2.

4. Pollen of the plant of claim 2.

5. Seed of an alfalfa plant pollinated by the pollen of claim 4.

6. An ovule of the plant of claim 2.

7. An alfalfa plant having all the physiological and morphological characteristics of the plant of claim 2.

8. The alfalfa plant of claim 2 that is male sterile.

9. A tissue culture of regenerable cells, the cells comprising genetic material from a synthetic variety alfalfa plant named WL-C290, wherein the cells regenerate plants having all the morphological and physiological characteristics of the synthetic alfalfa variety named WL-C290, the seed of which have been deposited and have ATCC Accession No. 209502.

10. A tissue culture of claim 9, comprising cultured cells from a plant part selected from the group consisting of leaves, roots, root tips, root hairs, anthers, pistils, stamens, pollen, ovules, flowers, seeds, embryos, stems, buds, cotyledons, hypocotyls, cells and protoplasts.

11. An alfalfa plant regenerated from the tissue culture of claim 9, having all the morphological and physiological characteristics of synthetic alfalfa variety WL-C290.

12. A method for producing first-generation synthetic variety alfalfa seed comprising crossing a first parent alfalfa plant with a second parent alfalfa plant and harvesting resultant first-generation (F1) hybrid alfalfa seed, wherein said first or second parent alfalfa plant is the alfalfa plant of claim 2.

13. Seed of one or more alfalfa plants, wherein the seed comprises genetic material derived from alfalfa variety designated WL-C290 and having ATCC Accession No. 209502 wherein said seed are produced by the method of claim 12.

14. The seed of claim 13, wherein the seed is produced by a cage-cross breeding program.

15. An alfalfa plant or its parts each produced by the seed of claim 13 or regenerable parts of said seed.

16. Seed of the alfalfa plant of claim 15.

17. An alfalfa plant produced by the seed of claim 13 or regenerable parts of said seed, wherein the plant has resistance to silverleaf whitefly.

18. A method for producing first-generation synthetic variety alfalfa seed comprising crossing a first parent alfalfa plant with a second parent alfalfa plant and harvesting resultant first-generation (F1) hybrid alfalfa seed, wherein said first or second parent alfalfa plant is the alfalfa plant of claim 7.

19. Seed of one or more alfalfa plants, wherein the seed comprises genetic material derived from alfalfa variety designated WL-C290 and having ATCC Accession No. 209502, wherein the seeds are produced by the method of claim 18, and wherein the seeds generate plants having all the morphological and physiological characteristics of an alfalfa plant produced by seed of synthetic alfalfa variety designated WL-C290 and having ATCC Accession No. 209502.

20. Seed of the alfalfa plant of claim 7.

21. A plant part of the alfalfa plant of claim 7.

22. A method for producing first-generation synthetic variety alfalfa seed comprising crossing a first parent alfalfa plant with a second parent alfalfa plant and harvesting resultant first-generation (F1) hybrid alfalfa seed, wherein said first or second parent alfalfa plant is the alfalfa plant of claim 11.

23. Seed of one or more alfalfa plants, wherein the seed comprises genetic material derived from alfalfa variety designated WL-C290 and having ATCC Accession No. 209502, wherein the seeds are produced by the method of claim 22, and wherein the seeds generate plants having all the morphological and physiological characteristics of an alfalfa plant produced by seed of synthetic alfalfa variety designated WL-C290 and having ATCC Accession No. 209502.

24. Seed of the alfalfa plant of claim 11.

25. A plant part of the alfalfa plant of claim 11.

26. A plant part of the alfalfa plant of claim 2.

* * * * *

UNITED STATES PATENT AND TRADEMARK OFFICE
CERTIFICATE OF CORRECTION

PATENT NO. : 6,143,951
DATED : November 7, 2000
INVENTOR(S) : Cluff et al.

It is certified that error appears in the above-identified patent and that said Letters Patent is hereby corrected as shown below:

Column 2,
Line 22, delete "707-365-2700." and insert -- 707-365-2700). --, therefor.

Column 11,
Line 23, delete "generate" and insert -- generates --, therefor.
Line 33, delete "2.8" and insert -- 2.5 --, therefor.
Line 33, delete "42.5" and insert -- 49.9 --, therefor.

Column 13, Table 6,
Line 12, delete "Meccall" and insert -- Mecca II --, therefor.

Column 18,
Line 22, insert -- that -- after "seed".

Column 20,
Line 34, delete "alfalfa," and insert -- alfalfa; --, therefor.

Claim 13,
Insert a comma after "209502".

Signed and Sealed this

Twenty-eighth Day of August, 2001

*Attest:*

NICHOLAS P. GODICI
*Attesting Officer*   *Acting Director of the United States Patent and Trademark Office*